United States Patent
Okamoto

(12) 
(10) Patent No.: US 9,375,135 B2
(45) Date of Patent: Jun. 28, 2016

(54) INSERTION DEVICE COMPRISING OPERATION INPUT PORTION

(71) Applicant: Olympus Corporation, Tokyo (JP)

(72) Inventor: Yasuhiro Okamoto, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 43 days.

(21) Appl. No.: 14/477,373

(22) Filed: Sep. 4, 2014

(65) Prior Publication Data

US 2014/0371534 A1 Dec. 18, 2014

Related U.S. Application Data

(63) Continuation of application No. PCT/JP2013/057711, filed on Mar. 18, 2013.

(30) Foreign Application Priority Data

Mar. 23, 2012 (JP) .................................. 2012-067553

(51) Int. Cl.
*A61B 1/00* (2006.01)
*A61B 1/005* (2006.01)
*G02B 23/24* (2006.01)

(52) U.S. Cl.
CPC .............. *A61B 1/0016* (2013.01); *A61B 1/0052* (2013.01); *A61B 1/0057* (2013.01); *A61B 1/00066* (2013.01); *G02B 23/2476* (2013.01)

(58) Field of Classification Search
CPC .......... A61B 1/00066; A61B 1/00068; A61M 25/0105; A61M 25/0133; A61M 25/0136; A61M 25/0147

USPC ............. 600/131, 146, 148, 150; 604/164.12, 604/528

See application file for complete search history.

(56) References Cited

U.S. PATENT DOCUMENTS 3,897,775 A * 8/1975 Furihata ............... A61B 1/0052
600/131
4,207,873 A * 6/1980 Kruy ..................... A61B 1/0052
600/146

(Continued)

FOREIGN PATENT DOCUMENTS

EP          2 229 868 A1    9/2010
JP          U-05-041501     2/1993

(Continued)

OTHER PUBLICATIONS

Jan. 7, 2014 Office Action issued in Japanese Patent Application No. 2013-547439 (with English translation.).

(Continued)

*Primary Examiner* — Anhtuan T Nguyen
*Assistant Examiner* — Jae Woo
(74) *Attorney, Agent, or Firm* — Oliff PLC

(57) ABSTRACT

An insertion device includes a UD knob having an outer peripheral side notched in a concave recess with such a curvature and a size as to come in close contact with a base part of a thumb, and an RL knob placed on the UD knob with the same center of rotation, and is configured such that the thumb extends beyond the UD knob, the base part of the thumb is put in contact with a deepest part of the recess of the UD knob, and the RL knob is operably present within a movable range of the thumb beyond the UD knob. The RL knob is configured to be driven by a motor, and thereby the RL knob is rotated by a fingertip to bend a bend portion.

9 Claims, 11 Drawing Sheets

(56) References Cited

U.S. PATENT DOCUMENTS

| | | | | |
|---|---|---|---|---|
| 4,557,554 | A | * | 12/1985 | Blanc ............... G02B 6/4298 353/52 |
| 4,702,432 | A | * | 10/1987 | Kaneko ............. A01K 89/027 242/246 |
| 5,060,632 | A | * | 10/1991 | Hibino ............. A61B 1/00039 348/65 |
| 5,439,522 | A | * | 8/1995 | Zejda ................ C23C 14/50 118/500 |
| 5,788,036 | A | * | 8/1998 | Soffa .................. F16D 23/06 192/110 R |
| 5,924,978 | A | * | 7/1999 | Koeda ............... G02B 6/0006 600/131 |
| 2002/0143238 | A1 | | 10/2002 | Hino et al. |
| 2004/0054254 | A1 | | 3/2004 | Miyake |
| 2006/0100484 | A1 | * | 5/2006 | Maeda ............... A61B 1/0051 600/146 |
| 2009/0163769 | A1 | * | 6/2009 | Robertson ......... A61B 1/00114 600/109 |
| 2010/0069834 | A1 | * | 3/2010 | Schultz ............. A61M 25/0136 604/95.04 |
| 2011/0065994 | A1 | | 3/2011 | Kudoh et al. |
| 2011/0088498 | A1 | | 4/2011 | Ettwein et al. |
| 2013/0060088 | A1 | * | 3/2013 | Okamoto ........... A61B 1/00066 600/146 |
| 2013/0072754 | A1 | * | 3/2013 | Okamoto ........... A61B 1/00105 600/109 |
| 2013/0190566 | A1 | * | 7/2013 | Miyoshi ............. A61B 1/0057 600/131 |
| 2013/0190567 | A1 | * | 7/2013 | Miyoshi ............. A61B 1/0052 600/137 |
| 2013/0303855 | A1 | * | 11/2013 | Masaki .............. A61B 1/0052 600/146 |
| 2013/0331652 | A1 | * | 12/2013 | Okamoto ............ A61B 1/0052 600/146 |
| 2013/0338441 | A1 | * | 12/2013 | Okamoto ............ A61B 1/0052 600/146 |
| 2014/0121462 | A1 | * | 5/2014 | Okamoto ............ A61B 1/0052 600/149 |
| 2014/0135580 | A1 | * | 5/2014 | Omoto ................ A61B 1/0052 600/148 |
| 2014/0200513 | A1 | * | 7/2014 | Koitabashi ......... A61B 1/00066 604/95.04 |
| 2014/0309625 | A1 | * | 10/2014 | Okamoto ............ A61B 1/0057 606/1 |

FOREIGN PATENT DOCUMENTS

| | | | |
|---|---|---|---|
| JP | 2004008342 | A * | 1/2004 |
| JP | A-2004-008342 | | 1/2004 |
| JP | A-2009-153959 | | 7/2009 |
| JP | 2009226125 | A * | 10/2009 |
| JP | A-2009-226125 | | 10/2009 |
| JP | A-2010-213969 | | 9/2010 |
| JP | A-2011-182981 | | 9/2011 |

OTHER PUBLICATIONS

Jul. 2, 2013 International Search Report issued in International Application No. PCT/JP2013/057711 (with English translation.).

Sep. 23, 2014 International Preliminary Report on Patentability issued in International Application No. PCT/JP2013/057711 (with English translation).

Nov. 26, 2015 Supplementary European Search Report issued in European Patent Application No. 13764985.1.

* cited by examiner

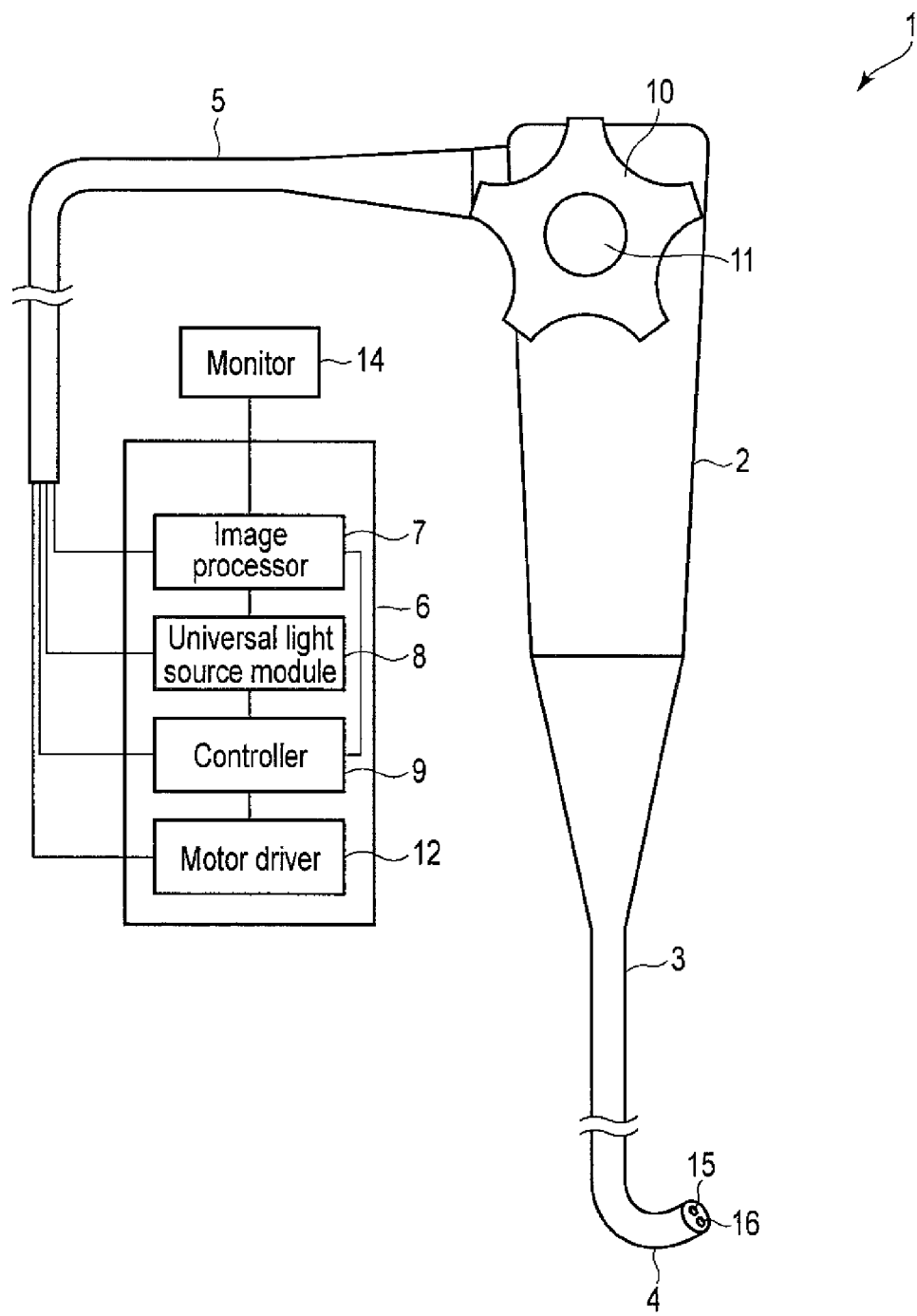
F I G. 1

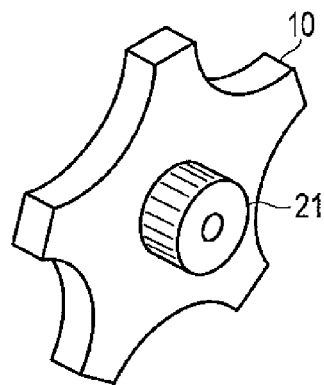
F I G. 3A
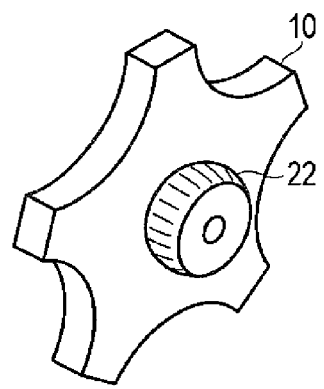
F I G. 3B
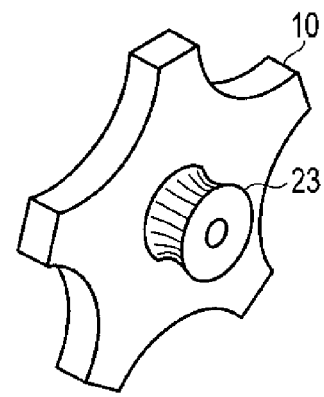
F I G. 3C

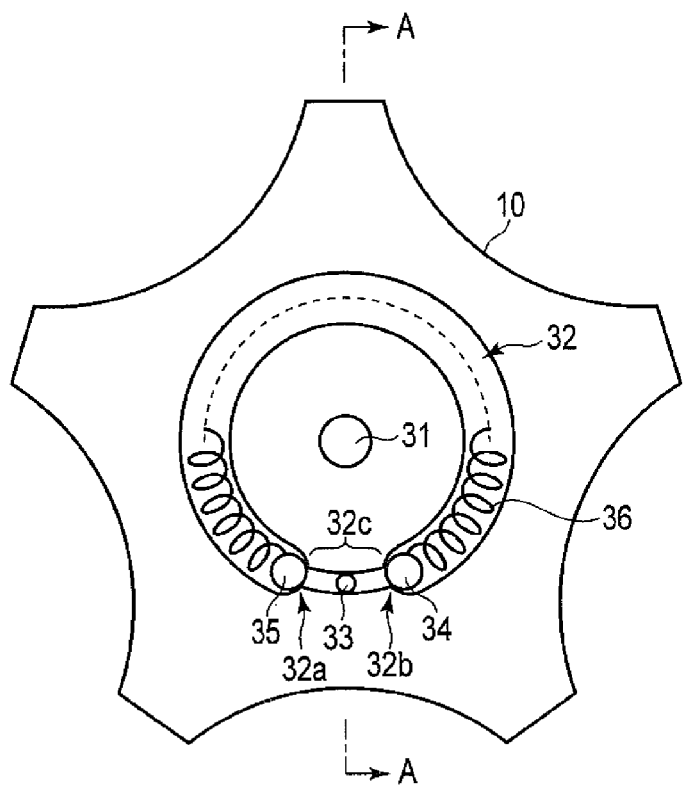
F I G. 4A
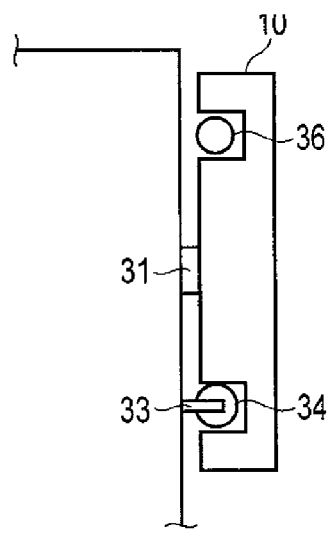
F I G. 4B

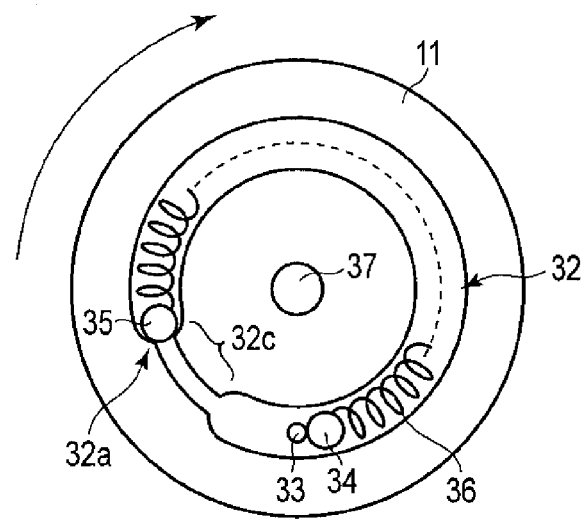
F I G. 4E
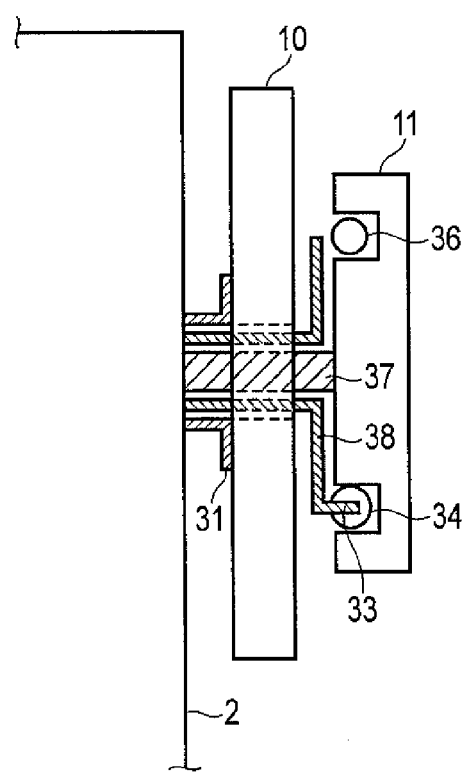
F I G. 4F

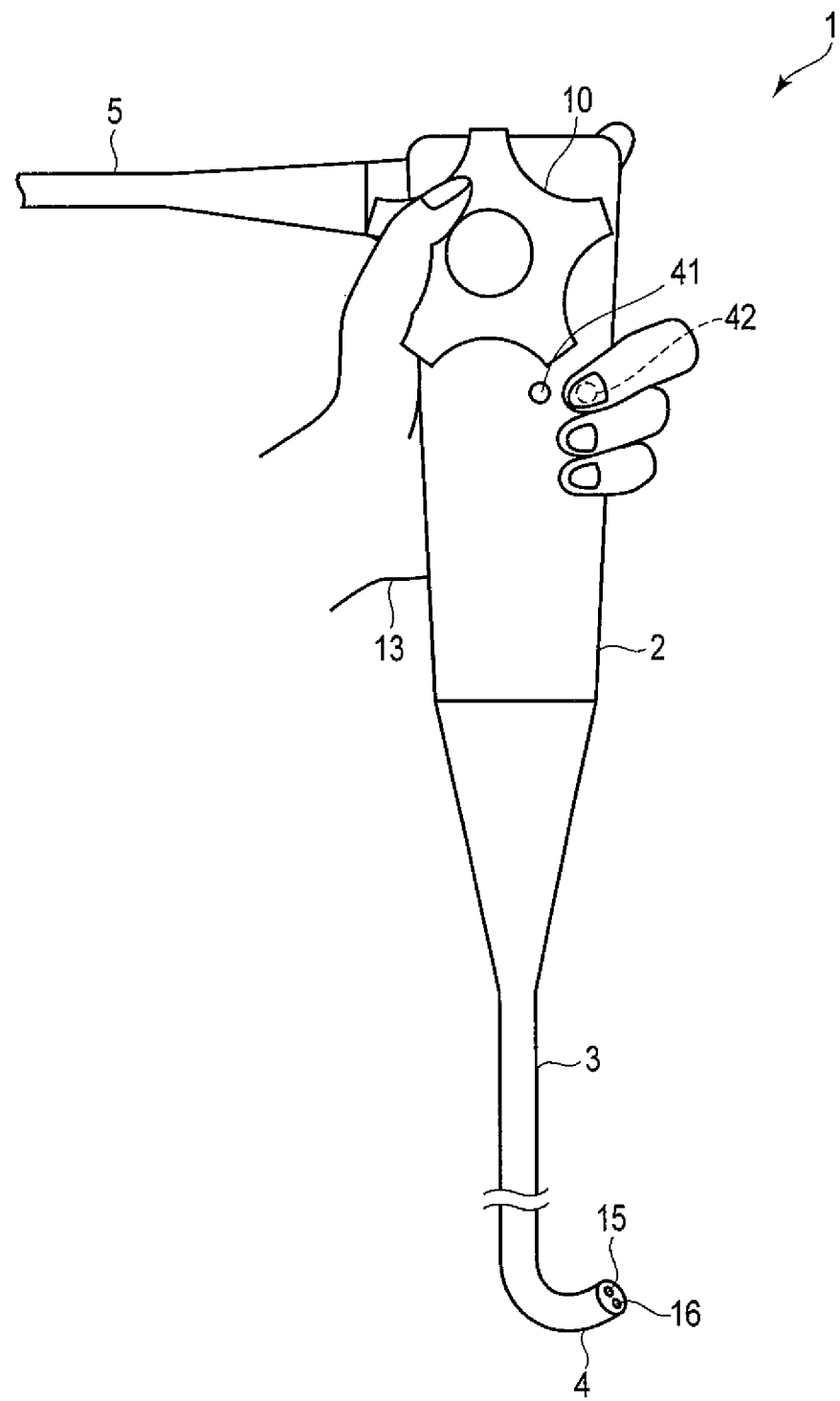
F I G. 5

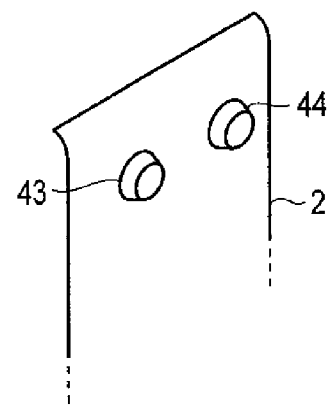
F I G. 6A
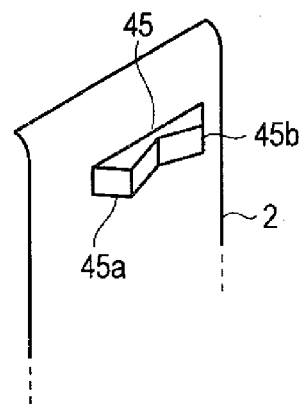
F I G. 6B
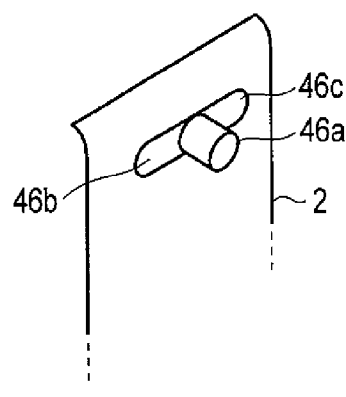
F I G. 6C

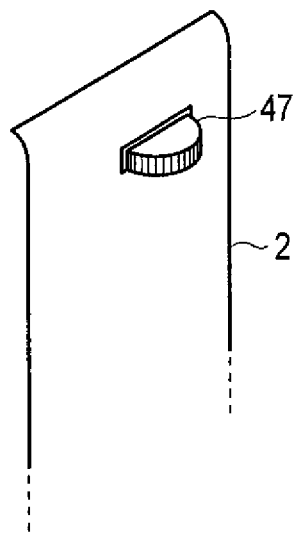
F I G. 6D
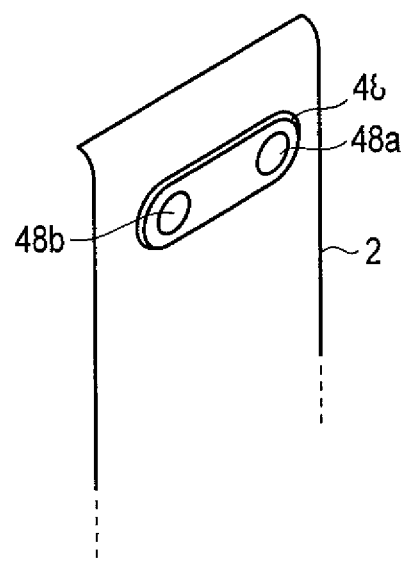
F I G. 6E

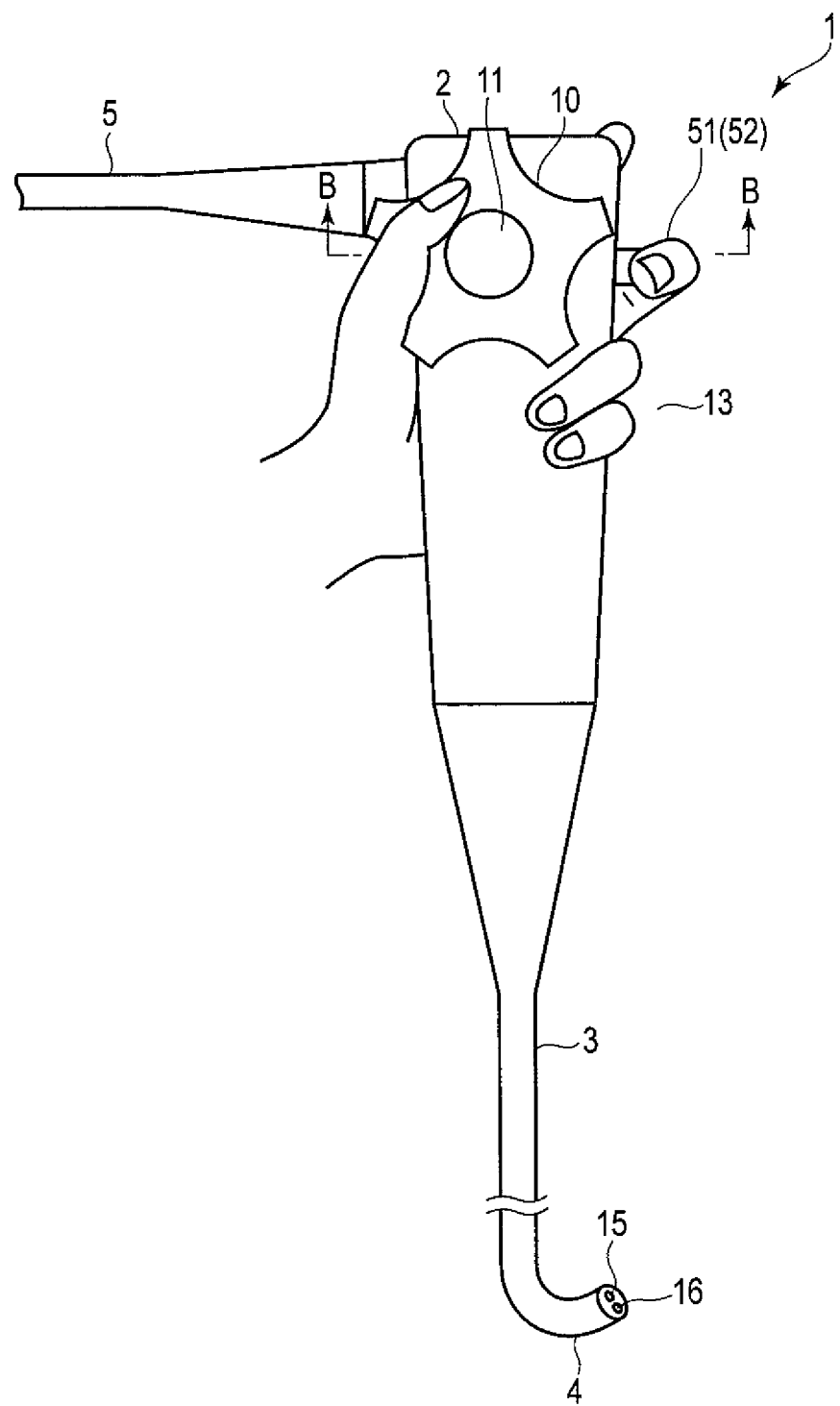
F I G. 7

INSERTION DEVICE COMPRISING OPERATION INPUT PORTION

CROSS-REFERENCE TO RELATED APPLICATIONS

This is a Continuation Application of PCT Application No. PCT/JP2013/057711, filed Mar. 18, 2013, which was published under PCT Article 21(2) in Japanese.

This application is based upon and claims the benefit of priority from prior Japanese Patent Application No. 2012-067553, filed Mar. 23, 2012, the entire contents of which are incorporated herein by reference.

BACKGROUND OF THE INVENTION

1. Field of the Invention

The present invention relates to an insertion device comprising an operation input portion for performing a bending operation of a bend portion.

2. Description of the Related Art

In an endoscope device which is publicly known as a general insertion device, a bend portion is disposed on a distal-end side of an insertion portion, and a forceps port, through which an image pickup portion and various therapeutic devices are passed, is provided in a distal-end surface of the bend portion. A bending operation is performed for the distal-end surface, for example, such that a desired observation target falls within an imaging visual field of the image pickup portion. This bending operation is performed by rotating an angle knob of an operation input portion which is provided on a proximal-end side of the insertion portion.

For example, as regards an operation input portion described in Jpn. UM Appln. KOKAI Publication No. H05-041501, there is disclosed a structure in which two knobs are placed on each other and are disposed on a main body of the operation input portion. Of these knobs, a UD knob, which is rotated within a certain angular range in order to perform a bending operation in an up/down direction, is disposed on the main body, and an RL knob, which has a smaller diameter than the UD knob and is rotated in order to perform a bending operation in a left/right direction, is disposed on an outside of the UD knob. The UD knob and RL knob are configured to have the same center of rotation.

The endoscope device is normally operated by both hands. An observer holds the operation input portion by one hand (usually, the left hand), and the UD knob and RL knob are rotated and operated by fingers. The other hand (right hand) holds the insertion portion, and performs advancement/retreatment and rotation of a distal end of the insertion portion, together with a bending operation.

The UD knob and RL knob in this Jpn. UM Appln. KOKAI Publication No. H05-041501 have such a polygonal shape that arcuate notches are provided on a peripheral edge, for instance, a star shape, which allows easy hooking of fingers. In addition, in Jpn. Pat. Appln. KOKAI Publication No. 2009-153959, first and second knobs, which are cylindrical, are proposed.

As has been described above, it is preferable that, basically, the operation input portion of the endoscope device, which is the insertion device, be held by one hand, and the knob operation be performed by a finger of this hand. Such an operation is not a difficult operation if the degree of skill is advanced. However, when the observer is not familiar with the operation, or when the size of the hold part of the operation input portion is slightly unsuited to the size of the hand due to a personal difference, such a situation would occur that the force of the finger for rotation is not exactly transmitted to the outer RL knob, and the knob operation is performed by taking the other hand off the insertion portion or by temporarily entrusting the holding of the insertion portion to another person.

In addition, the surface of the insertion portion of the endoscope device is coated with a member with elasticity of rubber or resin material. In the bend portion, if the observer rotates the knob, a force of pulling a wire, etc. acts, and the coating member is bent in a contracted state. Specifically, in the bend portion, such a force as to restore to the original extended state from the bent state acts by the elastic force, etc. of the coating member. Accordingly, when the observer takes the hand off the knob and sets the knob in a free state, the bend portion deforms in a manner to gradually extend to a halfway position from the bent state, and the observation target falls out of the imaging visual field. Although a fixing mechanism for fixing and holding is provided near the outer periphery of the UD knob, a fixing operation for the knob has to be performed each time. In addition, since a most part of the fixing mechanism of the RL knob is disposed on the RL knob, the fixing operation is performed by releasing the hand which holds the insertion portion.

In order to more finely advancing/retreating and rotating the distal end portion of the insertion portion in accordance with the rotation of the knob, without releasing the hand from the insertion portion at a time of the knob operation, there has been a demand from the observer that the insertion portion be moved by the observer himself/herself.

According to the present invention, there can be provided an insertion device comprising an operation input portion, which is held by one hand, can make easier a knob operation for bending a bend portion by a finger of the one hand, and can keep a bending state of the insertion portion.

BRIEF SUMMARY OF THE INVENTION

According to an embodiment of the present invention, there is provided an insertion device comprising: an insertion device comprising: an insertion portion provided with a bend portion which bends in a first axial direction and a second axial direction perpendicular to the first axial direction; a first rotary body with a first rotational shaft, the first rotary body configured to rotate about the first rotational shaft upon operation input for bending the bend portion in the first axial direction; a first wire fixed to the bend portion and configured to be pulled and bend the bend portion in the first axial direction; a first pulling mechanism coupled to the first rotational shaft and configured to pull the first wire in interlock with rotation of the first rotary body; a second rotary body with a second rotational shaft provided coaxially with the first rotational shaft, the second rotary body configured to rotate about the first rotational shaft upon operation input for bending the bend portion in the second axial direction; a second wire fixed to the bend portion and configured to be pulled and bend the bend portion in the second axial direction; a driving source configured to generate a driving force for bending the bend portion in the second axial direction; a rotation amount detector configured to detect a rotation amount of the second rotary body; a second pulling mechanism comprising a rotary portion attached the second wire to pull the second wire by rotating independently with respect to the second rotational shaft, the second pulling mechanism configured to pull the second wire in interlock with generation of the driving force by the driving source; and a controller configured to output to the driving source a driving signal for bending the bend portion in the second axial direction, based on the rotation amount detected by the rotation amount detector.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a view illustrating a conceptual configuration of a whole system including an operation input portion of an insertion device according to a first embodiment.

FIG. 3A is a view illustrating a structure example of the knob of the operation input portion.

FIG. 3B is a view illustrating a structure example of the knob of the operation input portion.

FIG. 3C is a view illustrating a structure example of the knob of the operation input portion.

FIG. 4A is a view conceptually illustrating a structure of a neutral position restoration mechanism provided in the knob of the operation input portion.

FIG. 4B is a view conceptually illustrating a structure of the neutral position restoration mechanism provided in the knob of the operation input portion.

FIG. 4E is a view illustrating a structure in a case where the neutral position restoration mechanism is provided in the RL knob.

FIG. 4F is a view illustrating a structure in a case where the neutral position restoration mechanism is provided in the RL knob.

FIG. 5 is a view illustrating an external-appearance structure of an operation input portion in which a bending speed adjuster is provided.

FIG. 6A is a view illustrating a structure example of a bending speed adjusting switch provided in the operation input portion.

FIG. 6B is a view illustrating a structure example of the bending speed adjusting switch provided in the operation input portion.

FIG. 6C is a view illustrating a structure example of the bending speed adjusting switch provided in the operation input portion.

FIG. 6D is a view illustrating a structure example of the bending speed adjusting switch provided in the operation input portion.

FIG. 6E is a view illustrating a structure example of the bending speed adjusting switch provided in the operation input portion.

FIG. 7 is a view illustrating an external-appearance structure of an operation input portion in which a state holding mechanism is mounted.

DETAILED DESCRIPTION OF THE PREFERRED EMBODIMENT

Embodiments of the invention will now be described in detail with reference to the accompanying drawings.

Figure 2:
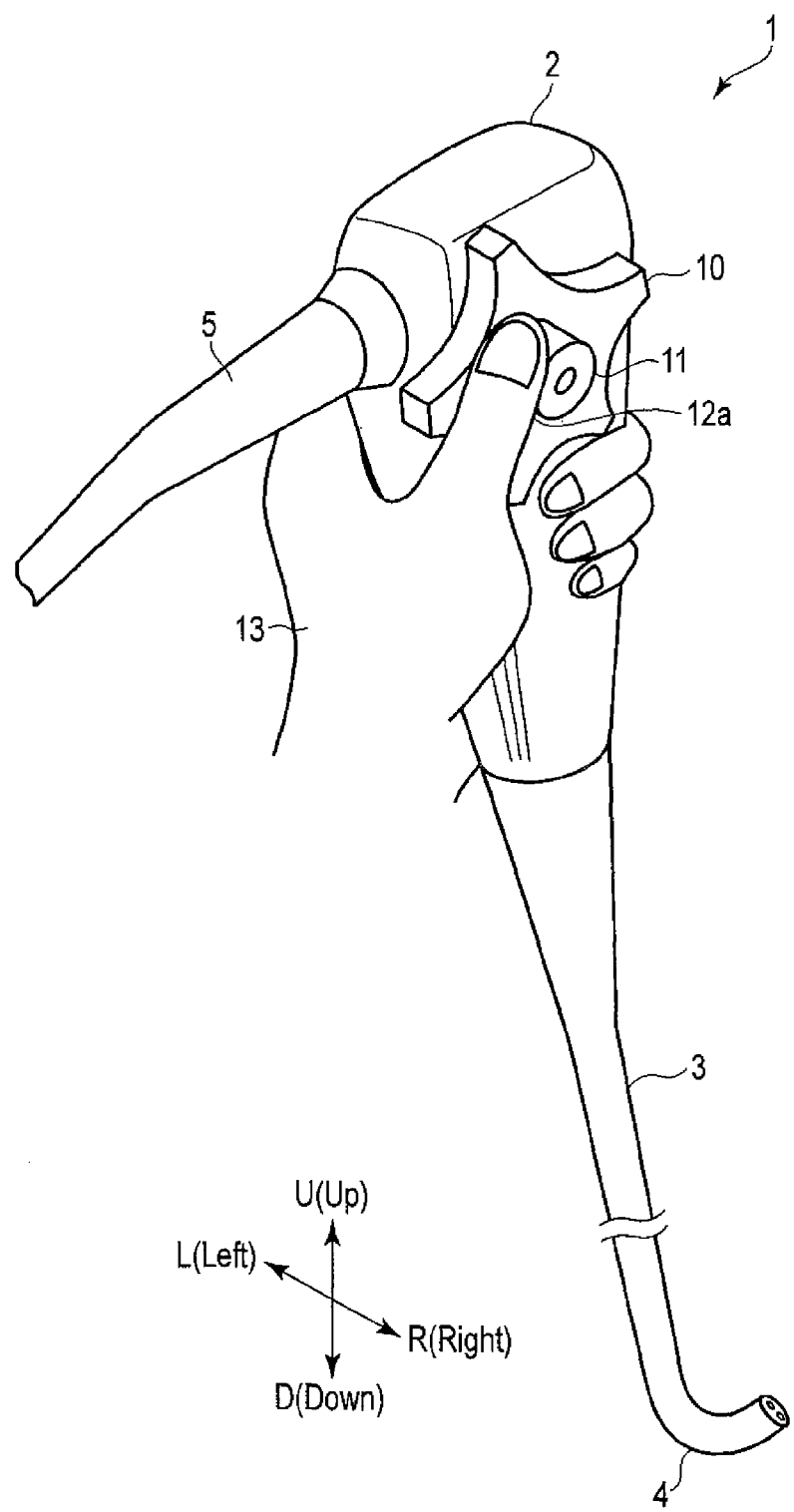
FIG. 2 is a view illustrating a state in which the operation input portion of the first embodiment is held by one hand, and a knob operation is being performed.

FIG. 1 is a view illustrating a conceptual configuration of a whole system including an operation input portion of an insertion device according to an embodiment. FIG. 2 is a view illustrating a state in which the operation input portion of the first embodiment is held by one hand, and a knob operation is being performed.

The present system is composed mainly of an endoscope body 1 which is an insertion device, and a driving control device 6. The endoscope body 1 is composed of an insertion portion 3 which is inserted in a lumen, a bend portion 4 provided on a distal-end side of the insertion portion 3, an operation input portion 2 provided on a proximal-end side of the insertion portion 3, and a universal cable 5 including a light guide fiber (or an optical fiber cable) which is a light guide path of illumination light, and a signal cable. An image pickup portion (objective lens) 15 and an illumination window 16 of illumination light are disposed on a distal-end surface of the bend portion 4. In addition, although not illustrated, a through-hole for insertion of a therapeutic device such as a forceps, which penetrates from the proximal-end side to the distal-end side, is opened, and a cleaning nozzle for cleaning the objective lens 15 is also disposed.

The driving control device 6 is composed of an image processor 7 which applies various image processes to a video signal of an observation target which has been imaged by the image pickup portion 15, a universal light source module 8 which generates illumination light which is emitted from the illumination window 16 through the light guide fiber (not shown), a controller 9 which executes control of the entirety of the endoscope device, including driving control of structural parts provided in the image pickup portion 15 and operation input portion 2, and a motor driver 12 which supplies driving power for driving a motor (to be described later) provided within the operation input portion 2. Furthermore, there are provided a monitor 14 which displays an image of an observation target, which has been processed by the image processor 7, and an input device such as a keyboard (not shown). Incidentally, there is no need to provide the motor driver 12, in a case where the bending operation by an RL knob 11 (to be described later) is performed by a manual method.

In FIG. 1 and FIG. 2, an operation input portion body of the operation input portion 2 has a bat-like oblong shape for easy holding. The universal cable 5 is connected to an upper-side surface of the operation input portion body, and a proximal-end portion of the bend portion 4 is coupled to a lower end of the operation input portion body. In addition, on an upper side of the front surface, there is disposed a UD knob (first operation input portion) with a star shape, which is rotated in order to perform a bending operation in an up/down direction that is a first axial direction. At a center of the outer side of the UD knob, there is disposed an RL knob (second operation input portion) 11 with a cylindrical shape, which is rotated in order to perform a bending operation in a left/right direction that is a second axial direction perpendicular to the first axial direction. The UD knob 10 and RL knob 11 are configured to have the same center position of rotation.

Although not illustrated, a plurality of wires are provided in the bend portion 4, and the respective wires are coupled at one end to a plurality of bend pieces which constitute the bend portion 4, and are passed, at the other end, over pulleys (not shown) disposed within the operation input portion 2. In the present embodiment, a bending mechanism, which is composed of the plural pulleys and wires, is included in the operation input portion body. By rotating the pulleys in interlock with the rotation of the knob and pulling the wires, the bend pieces are pulled and the bend portion 4 is bent.

The UD knob 10 of the embodiment is of the manual type. In the operation input portion 2, the pulley for bend driving in the up/down direction is coupled to a rotational shaft of the UD knob 10, and rotates in accordance with the rotational operation of the knob and pulls the wire. Incidentally, a gear (numeral 55 in FIG. 8) may be interposed between the UD knob 10 and the pulley, and the operational ratio between the rotational operation of the knob and the rotation of the pulley may be adjusted. In addition, if the RL knob 11 of the embodiment is of the manual type, the RL knob 11 has the same structure as the UD knob 10.

A description is given of the configuration at a time when the RL knob 11 of the embodiment is of a motor-driving type using a motor as a driving source. In the operation input portion 2, the pulley for bend driving in the left/right direction is equipped with a motor (or a motor driving source) which is not shown, such that the pulley and motor are meshed via a gear interposed. Specifically, the motor generates a driving force to bend the bend portion 4 in the left/right direction, rotates the pulley, and pulls the wire. The RL knob 11 functions as a switch, for instance, a rotary switch, for adjusting the supply power that is applied to the motor. Accordingly, by a slight rotational operation of the knob, the voltage (or current) that is supplied to the motor is adjusted in accordance with the amount of rotation, and the motor driving is controlled. For example, using a rotation detector (potentiometer, encoder, etc.) which detects a rotational angle, the rotational angle about the rotational axis of the RL knob 11 is detected, and the controller 9 outputs, in accordance with this rotational angle, a voltage (or current) for bending the bend portion 4 in the left/right direction to the motor as a driving signal. In the meantime, in the driving control of the motor, such control is executed by the controller 9 that even if the observer has suddenly rotated the RL knob 11, the bending operation does not temporally follow such rotation and the bending operation is slowly performed.

As regards the operation input portion 2, as illustrated in FIG. 2, the thumb (first finger) of one hand (left hand in this example) 13 is hooked on the UD knob 10 and RL knob 11, the middle finger (third finger), ring finger (fourth finger) and little finger (fifth finger), which extend beyond the back side of the body, hold the operation input portion body, and the index finger (second finger), not shown, is put on the back side of the body, thus stabilizing the hold state. Incidentally, although not illustrated in FIG. 1 and FIG. 2, in a case where a suction button or an air-feed/water-feed button are provided on the operation input portion, the index finger is in charge of the operations thereof.

The UD knob 10 of the embodiment has a disc shape with a plurality of recesses which are each notched in a recess (arcuate) shape toward the center of rotation from the outer peripheral side. These recesses are each formed with such a curvature (in this example, indicative of the degree of curvature of a curved surface) and a size as to be suited to close contact with the base of the thumb. In addition, the center position of rotation of the RL knob 11, relative to the operation input portion body, is set such that a deepest part of this recess agrees with, or is in the vicinity of, the position of the side surface of the operation input portion body. This aims at utilizing the movable range of the thumb to the maximum, with the base of the thumb being in contact with the deepest part of the recess.

Further, as regards the setting of the center position of rotation of the RL knob 11, it is necessary that the RL knob 11 be operably present within the movable range of the thumb beyond the UD knob 10. On the basis of the movable range of the thumb, the diameter, thickness and rotational position of the UD knob 10 are determined and, in addition, the diameter and the height of the side surface of the RL knob 11 are determined. Detailed numerical values of these are matters of design. Incidentally, although FIG. 2 shows a so-called star shape with five recesses (recessed curved shapes), the number of recesses is not limited.

In this hold state, the holding by the thumb is such that the second phalanx (proximal phalanx) between the base of the finger and the first joint is hooked on the UD knob 10, and the part from the inside to tip of the first phalanx (distal phalanx) on the distal side of the first joint is hooked on the RL knob 11. Specifically, in this state, the thumb is positioned to extend beyond the UD knob 10, and the tip of the thumb is hooked on the RL knob 11. As regards the operation of the UD knob 10 and RL knob 11 by the thumb, the second phalanx is hooked on the UD knob 10, and the UD knob 10 is rotated by swinging the base part of the thumb. At this time, if the state of the RL knob 11 is held by a holding mechanism (to be described later), the bent state of the bend portion in the left/right direction is kept even if the finger is released from the RL knob 11. In addition, the RL knob 11 is rotated by hooking the inside part or the tip of the first phalanx of the thumb and bending and stretching the first joint.

FIG. 3A to FIG. 3C illustrate modifications of the shape of the RL knob 11.

An RL knob 21 illustrated in FIG. 3A is configured such that concave and convex lines for preventing a slip are formed, or groove lines are cut, in the entirety of a cylindrical side surface of the above-described RL knob 11. An RL knob 22 illustrated in FIG. 3B is configured such that the cylindrical side surface of the RL knob 11 forms a barrel shape with a convex curved surface, and concave and convex lines for preventing a slip are formed, or groove lines are cut, in the cylindrical side surface. An RL knob 23 illustrated in FIG. 3C is configured such that the cylindrical side surface of the RL knob 11 forms a so-called hourglass shape with a concave curved surface, and concave and convex lines for preventing a slip are formed, or groove lines are cut, in the cylindrical side surface. As regards the slip prevention processing, aside from the concave and convex lines or the groove lines, many minute dot-shaped projections may be formed on the cylindrical side surface. Conversely, many minute holes may be formed on the cylindrical side surface. Besides, the cylindrical side surface of the RL knob 21 may be covered with a member of, e.g. rubber, on which a slip hardly occurs. However, it is necessary that the member have resistance to cleaning or sterilization.

As described above, by applying the slip prevention process to the RL knob, the hooking of the finger becomes better, and a fine operation becomes easy. In addition, by forming the convex surface as the surface with which the finger comes in contact, the pressing of the finger is performed in a point-by-point fashion, and the RL knob 22 becomes easy to rotate. Furthermore, by forming the concave surface as the surface with which the finger comes in contact, the contact area of the finger becomes large, and the RL knob 22 can be rotated with light pressing.

Figure 4C:
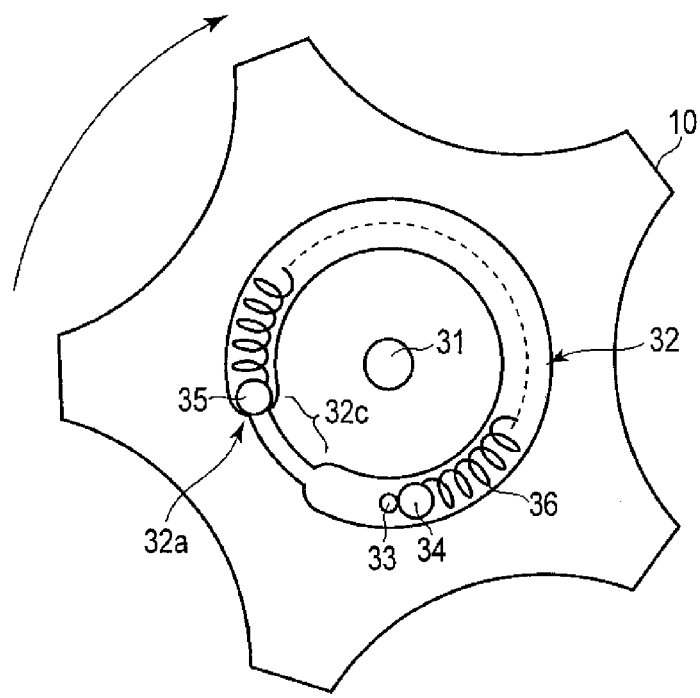
FIG. 4C is a view conceptually illustrating a structure of the neutral position restoration mechanism provided in the knob of the operation input portion.

FIG. 4A to FIG. 4F are views conceptually illustrating the structure of a neutral position restoration mechanism provided in the UD knob 10 of the operation input portion. FIG. 4B is a view illustrating a cross-sectional structure taken along line segment A-A in FIG. 4A. Incidentally, in the above-described knobs 11, 21, 22 and 23, too, the same mechanism as the neutral position restoration mechanism provided in the UD knob 10 can be provided. In this description, the UD knob 10 is described by way of example. A neutral position of the bend portion, in this context, means a position in a state in which the bend portion is extended substantially straight. In this embodiment, the neutral position is set as a preset range (a middle position region: narrow-width groove 32*c* to be described later) including the center position.

In the case where the observer inserts the insertion portion in a lumen and repeats a knob operation by reciprocally rotating the UD knob 10, the observer becomes unable to understand the present bent state of the bend portion of the insertion portion. Thus, a mechanism is needed for restoring the bent portion to a neutral position, that is, a state in which the bent portion extends straight.

As illustrated in FIG. 4A and FIG. 4B, in this neutral position restoration mechanism, an annular groove 32 having a center at a rotational shaft 31 is formed in the UD knob 10, on the surface side opposed to the operation input portion body. In this annular groove 32, a narrow-width groove 32*c* is formed as a middle position region with a partly narrowed width, that is, a range (allowance region) in which the bend portion 4 extends substantially straight. At the central position of the range of this narrow-with groove 32*c*, a columnar fixing pin 33 is erectingly provided on the body side of the operation input portion 2. At the position of this fixing pin 32, the central position of the bend portion is defined. Further, moving spherical bodies 34, 35 are disposed at end portions 32*a*, 32*b* in the annular groove 32. Between these spherical bodies, a coil spring 36 which urges in a manner to extend is fitted in the annular groove 32.

In this structure, as illustrated in FIG. 4C, when the UD knob 10 has been rotated in the direction of an arrow about the rotational shaft 31, the moving spherical body 35 is pushed by the end portion 32*a* and is moved together as one body. On the other hand, the moving spherical body 34 is pushed by the coil spring 36 as the end portion 32*b* rotates, and the moving spherical body 34 abuts on the fixing pin 33 and enters a resting state. Thus, as the UD knob 10 is rotated further, the coil spring 36 is contracted and the urging force increases. In this case, if the hand is released from the UD knob 10, the moving spherical body 35 together with the end, portion 32*a* is pushed back by the urging force of the coil spring 36 in a direction opposite to the direction of the arrow, and is returned to the state illustrated in FIG. 4A. The coil spring 36 adopted in this embodiment is formed by taking into account the choice of material, spring characteristics, etc., so that the coil spring 36 may slowly extend even when it is greatly contracted. In addition, the UD knob 10 has a neutral position corresponding to a neutral state of the bend portion 4 (a state in which the bend portion 4 becomes substantially straight). After the bend portion 4 is bent in the up/down direction, the UD knob 10 slowly restores from the rotational position of the UD knob 10, from which the hand has been released, toward the neutral position of the UD knob 10 by receiving the action of the restoration force (e.g. the urging farce produced by the coil spring 36) for restoring the UD knob 10 to the neutral position, this restoration force being produced by the above-described neutral position restoration mechanism, that is, by the elastic member (e.g. coil spring 36, spiral spring) provided in the neutral position restoration mechanism. Accordingly, the bend portion 4, which has been bent in the up/down direction, restores slowly to the neutral position.

Figure 4D:
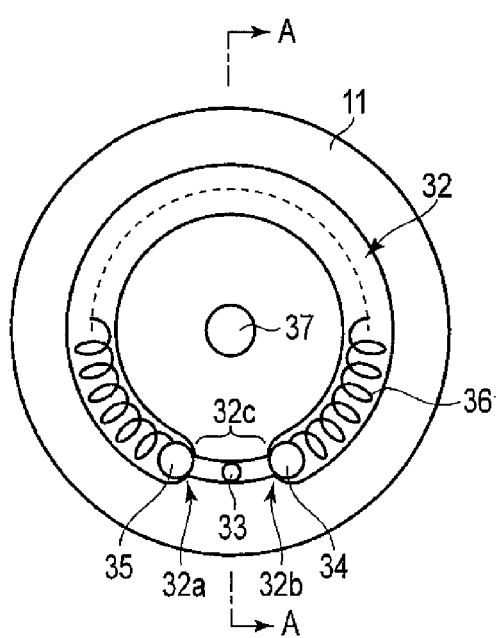
FIG. 4D is a view illustrating a structure in a case where the neutral position restoration mechanism is provided in an RL knob.

FIG. 4D to FIG. 4F are views illustrating a structure in a case where the above-described neutral position restoration mechanism is provided in the RL knob 11. As regards the structural elements of the neutral position restoration mechanism in FIG. 4D to FIG. 4F, a fixing member 38 and a rotational shaft 37 are added to the same structural elements as those of the neutral position restoration mechanism illustrated in FIG. 4A to FIG. 4C. The fixing member 38 fixes the fixing pin 33 to the body side of the operation input portion 2. The rotational shaft 37 is fixed to the RL knob 11, and rotates together with the rotation of the RL knob 11.

As illustrated in FIG. 4F, a hole, through which the fixing member 38 can be inserted, is provided in the rotational shaft 31. In addition, a hole, through which the rotational shaft 37 can be inserted, is provided in the fixing member 38. The fixing member 38 is inserted in the hole of the rotational shaft 31, and one end thereof is fixed to the body side of the operation input portion. The fixing pin 33, which is engageable with the narrow-width groove 32*c*, is provided on the fixing member 38 which extends from a stationary portion fixed on the body side of the operation input portion 2, is inserted in the hole provided along the rotational shaft 31 in the UD knob 10, and projects from the UD knob 10. Specifically, the fixing pin 33 is fixed to the operation input portion 2 via the fixing member 38. In addition, the rotational shaft 37 is inserted in the hole of the fixing member 38, and is attached to the body side of the operation input portion 2 such that the rotational shaft 37 is rotatable on the inner peripheral surface of the hole of the fixing member 38. The fixing member 38 fixes the fixing pin 33 such that the fixing pin is located at the central position of the narrow-width groove 32*c* at a time when the RL knob 11 is in the neutral position.

As illustrated in FIG. 4E, when the RL knob 11 has been rotated in the direction of an arrow about the rotational shaft 37 in the fixing member 38, the moving spherical body 35 is pushed by the end portion 32*a* and is moved together as one body. On the other hand, the moving spherical body 34 is pushed by the coil spring 36 as the end portion 32*b* rotates, and the moving spherical body 34 abuts on the fixing pin 33 and enters a resting state. Thus, as the RL knob 11 is rotated further, the coil spring 36 is contracted and the urging force increases. In this case, if the hand is released from the RL knob 11, the moving spherical body 35 together with the end portion 32*a* is pushed back by the urging force of the coil spring 36 in a direction opposite to the direction of the arrow, and is returned to the state illustrated in FIG. 4D. The coil spring 36 adopted in this embodiment is formed by taking into account the choice of material, spring characteristics, etc., so that the coil spring 36 may slowly extend even when it is greatly contracted. In addition, the RL knob 11 has a neutral position corresponding to a neutral state of the bend portion 4 (a state in which the bend portion 4 becomes substantially straight). After the bend portion 4 is bent in the left/right direction, the RL knob 11 slowly restores from the rotational position of the RL knob 11, from which the hand has been released, toward the neutral position of the RL knob 11 by receiving the action of the restoration force (e.g. the urging force produced by the coil spring 36) for restoring the RL knob 11 to the neutral position, this restoration force being produced by the elastic member (e.g. coil spring 36, spiral spring) provided in the above-described neutral position restoration mechanism. Accordingly, the bend portion 4, which has been bent in the left/right direction, restores slowly to the neutral position.

As has been described above, according to the present embodiment, by the thumb operation of one hand holding the operation input portion of the endoscope, the rotational operations of both the UD knob 10 and RL knob 11 can easily be performed at the same time. In addition, since the RL knob 11 is the structural part functioning as the electrical switch of the motor, compared to a manual RL knob RL, the load on the rotational operation is lighter, and the operation can easily be performed by the first phalanx or the fingertip. Therefore, the above-described neutral position restoration mechanism is suitably provided on the electrical switch for driving the bend portion 4.

Although the description has been given of the structure in which the neutral position restoration mechanism is provided in each of the UD knob 10 and RL knob 11, it is preferable to provide the neutral position restoration mechanism on, in particular, the RL knob 11, in the case of the endoscope, as in the embodiment of FIG. 1 and FIG. 2, which is provided with the UD knob 10 which manually bends the bend portion 4 in the up/down direction, and the RL knob 11 functioning as the electrical switch for bending the bend motor 4 in the left/right direction by the motor. Even by providing the above-described neutral position restoration mechanism on only the RL knob 11, it is possible to make easier the estimation of the bending state of the bend portion by the observer. In addition, in the case where the neutral position restoration mechanism is provided in each of the UD knob 10 and RL knob 11, even when the observer has repeatedly rotated the UD knob 10 and RL knob 11, the bend portion can slowly restore to the straight extended state that is the neutral position, by releasing the knobs. Thereby, the observer can easily estimate the bending state of the bend portion.

FIG. 5 is a view illustrating an external-appearance structure of an operation input portion in which a bending speed adjuster is provided. FIG. 6A to FIG. 6E are views illustrating structure examples of a bending speed adjusting switch provided in the operation input portion. In a structure of this embodiment, a speed adjuster for a motor is provided in the operation input portion 2 and controller 9, and the bending speed of the bend portion 3 is controlled.

The control of the bending speed of the bend portion 3 of the endoscope device has conventionally been executed by operating a speed adjusting switch which is provided in the universal light source module 8 or the controller 9. Thus, the observer himself/herself executes a switching operation by suspending observation, or the observer gives, from time to time, an instruction to the staff in the vicinity of the switch. This takes a lot of labor, and such a situation is expected that time is consumed for this operation.

As illustrated in FIG. 5, bending speed adjusting switches 41, 42, which instruct an increase or a decrease in rotational speed of the motor, are provided under the UD knob 10 of the operation input portion 2. These switches 41, 42 are connected by wire to the controller 9 via the universal cable 5. The controller 9, which has received a switch operation, controls the motor driver 12 and adjusts the rotation of the motor provided in the operation input portion body, and thereby the bending speed is controlled. If these switches 41, 42 are not pressed, the motor is driven at a preset rotation speed (initial rotation speed).

In these switches 41 and 42, for example, the rotation speed of the motor is linearly decelerated by pressing the switch 41 in accordance with the time of pressing (count time), and, conversely, the rotation speed of the motor is linearly accelerated by pressing the switch 42 in accordance with the time of pressing. When the hand is released from each switch 41, 42, the rotation speed of the motor is restored to the preset rotation speed.

In a method other than this speed adjusting method, when the hand has been released from each switch 41, 42, the accelerated or decelerated rotation speed of the motor at that time is maintained. Such setting may be executed that when the rotation speed has been varied by the switch 41, the rotation speed is reset by the pressing of the switch 42, and the rotation speed is restored to the initial rotation speed. Conversely, when the rotation speed has been varied by the switch 42, the rotation speed may be reset by the pressing of the switch 41, and the rotation speed may be restored to the initial rotation speed. As regards these speed adjusting methods, various methods are applicable by changing the program of the controller.

FIG. 6A to FIG. 6E are views illustrating structure examples of the bending speed adjusting switch provided in the operation input portion. Basically, switches which perform momentary operations are adopted as the bending speed adjusting switches to be described below. Incidentally, the bending speed, that is, the adjustment of increasing/decreasing the rotational speed of the motor, is performed within a preset range of acceleration, and the upper and lower limits of the speed are set.

Switches 43 and 44 illustrated in FIG. 6A are press-button-type switches. These switches are the same as the above-described switches 41 and 42, and are an acceleration switch 43 and a deceleration switch 44 of the rotational speed, respectively. Needless to say, these switches may be disposed at transposed positions.

A switch 45 illustrated in FIG. 6B is a so-called rocker-type switch which is supported at a central part thereof and swings (seesaw operation). When each of both ends is pressed, the switch is turned on. As illustrated, a neutral position is a normal position and is an OFF state. For example, when a switch terminal 45a of the switch 45 is pressed, the rotational speed of the motor is linearly decelerated in accordance with the pressing time (count time). Conversely, when a switch terminal 45b is pressed, the rotational speed of the motor is linearly accelerated in accordance with the pressing time. When the hand has been released from either switch terminal 45a, 45b, the switch is restored to the neutral position in FIG. 6B by an urging member (not shown), and the rotational speed of the motor is restored to a preset rotational speed.

A switch 46 illustrated in FIG. 6C is a slide switch. In this slide switch 46, for example, when a lever 46a is slid to a slide end 46b, the rotational speed of the motor is linearly decelerated in accordance with a time (count time) during which the lever 46a has been shifted. Conversely, when the lever 46a is slid to a slide end 46c, the rotational speed of the motor is linearly accelerated in accordance with the time during which the lever 46a has been shifted. When the hand has been released from the lever 46a, the lever 46a moves back to the neutral position shown in FIG. 6C by an urging member (not shown), and the rotational speed of the motor is restored to a preset rotational speed. In this example, the rotational speed is accelerated or decelerated in accordance with the time during which the slide switch has been shifted to the end. However, the rotational speed may be adjusted in accordance with a distance from the central position to a position where the slide switch has been shifted.

A switch 47 illustrated in FIG. 6D is a rotary-type switch. This switch 47 is configured such that, for example, a disc-shaped rotational portion is rotatably supported inside the operation input portion 2, and a part of the rotational portion is exposed. A slip prevention process by concave and convex lines is applied to a side surface of the switch 47.

In this switch 47, for example, when the rotational portion has been rotated in a CW direction (clockwise direction), the rotational speed of the motor is linearly decelerated in accordance with the amount of rotation of the rotational portion. Conversely, when the rotational portion has been rotated in a CCW direction (counterclockwise direction), the rotational speed of the motor is linearly accelerated in accordance with the amount of rotation of the rotational portion. When the hand has been released from the rotational portion, the rotational portion returns to the neutral position shown in FIG. 6D by an urging member (not shown), and the rotational speed of the motor is restored to a preset rotational speed.

A switch 48 illustrated in FIG. 6E is a touch-type switch configured such that publicly-known pressure-sensing switches, in each of which a pair of electrodes are disposed to face each other, are arranged. In this switch 48, for example, when a pressure-sensing switch (switch portion) 48a has been touched, the rotational speed of the motor is linearly decelerated in accordance with the time of contact. Conversely, when a pressure-sensing switch 48b has been touched, the rotational speed of the motor is linearly accelerated in accordance with the time of contact. When the hand has been released from the pressure-sensing portion 48a, 48b, the switch enters an OFF state, and the rotational speed of the motor is restored to a preset rotational speed.

As has been described above, according to the present embodiment, the bending speed adjusting switch is disposed on the operation input portion 2. Thereby, the observer can adjust the bending speed to a desired speed, and when an observation target is to be searched or to be observed with attention, a proper speed of movement can be set in accordance with the condition of observation.

In addition, since the bending speed adjusting switch is disposed under the CD knob 10 of the operation input portion 2, the operation can be performed by the third finger in the state in which the operation input portion 2 is being held.

Figure 8:
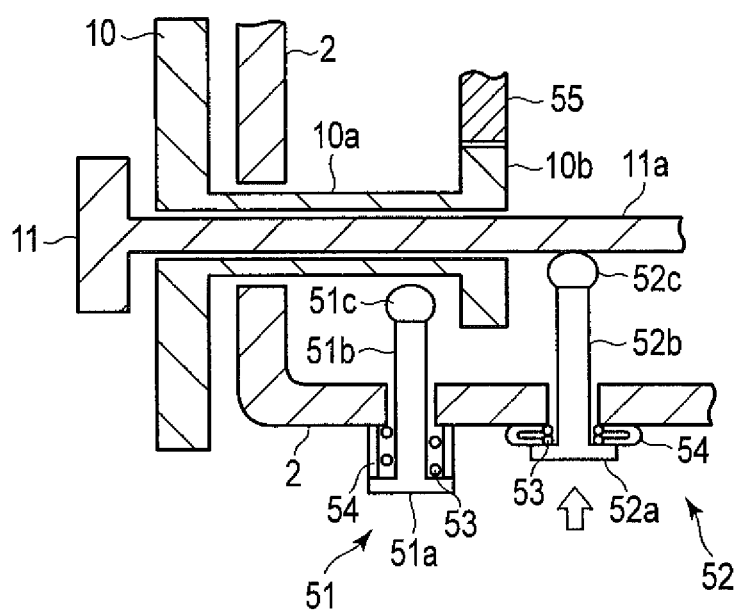
FIG. 8 is a view illustrating a structure example of the state holding mechanism provided in the operation input portion.

FIG. 7 is a view illustrating an external-appearance structure of an operation input portion in which a holding mechanism for holding a bending state is mounted. FIG. 8 is a view illustrating a conceptual structure example of the holding mechanism provided in the operation input portion.

In the case of the UD knob 10 and RL knob 11 provided with the above-described neutral position restoration mechanism, if the hand is released from the knob, the bending portion is automatically restored to the neutral position. When the observer performs endoscopic observation, there occurs such a situation that the observer temporarily fixes the bending state and views an observation image. In this case, the observer has no choice but to keep at rest the thumb which is hooked on the UD knob 10 and RL knob 11.

This being the case, the holding mechanism illustrated in FIG. 7 and FIG. 8 is provided in the operation input portion. As illustrated in FIG. 8, push-type lock buttons 51 and 52, which fix the UD knob 10 and RL knob 11, respectively, are juxtaposed on an upper part of a side surface of the operation input portion 2 (a surface opposite to the surface to which the universal cable 5 is coupled).

The lock buttons 51, 52 have functions of locking, when the lock buttons 51, 52 are pressed down, the rotational shafts of the UD knob 10 and RL knob 11 so that the UD knob 10 and RL knob 11 may not rotate.

As illustrated in FIG. 8, for example, the lock button 51 itself is formed of an operation surface 51a and a shaft portion 51b which are formed of a resin material, and an engaging portion 51c which is attached to the shaft portion 51b and is formed of an elastic material such as rubber. The operation surface 51a and shaft portion 51b are formed of a resin as one piece. At the part exposed from the armor member of the operation input portion 2, a spring 53 is fitted on the shaft portion 51b under the operation surface 51a, and these are covered with a cover 54. Similarly, the lock button 52 is formed of an operation surface 52a, a shaft portion 52b and an engaging portion 52c, and is provided with a spring 53 and a cover 54.

In this structure, as illustrated in FIG. 8, if the lock button 52 is pushed by the finger, the spring 53 is compressed and the engaging portion 52c is pressed on the rotational shaft 11a of the RL knob 11. The engaging portion 52c elastically deforms to come in contact with the rotational shaft 11a, thereby holding the rotational shaft 11a from rotating. By this holding of the rotational shaft 11a, the rotation of the pulley, with which the rotational shaft 11a is engaged, is fixed, the moving of the wire is stopped, and the bending state of the bend portion 4 is kept. Thereby, the bending state of the bend portion 4 is locked. In addition, if the finger is released from the lock button 52, the operation surface 52a is pushed up by the urging force of the spring 53, and the engaging portion 52c is separated from the rotational shaft 11a. Thereby, the bending state of the bend portion 4 is released.

In this example, the lock button 51, 52 is not provided with a mechanism which keeps or releases the pushed state of the button when the button has been pushed. However, such a configuration may be adopted that a mechanism by a publicly-known rotary cam method or a ratchet cam method is added so that an alternate operation may be performed.

As has been described above, with the holding mechanism of this embodiment, the bending state of the bend portion can temporarily be fixed by a one-hand operation. Thus, at a time of observation, where necessary, a still captured image can be observed. In addition, if the bending state of the bend portion is temporarily fixed and maintained, the hand can be released from the knob.

Furthermore, in the holding mechanism, the lock buttons are disposed at a position opposed to the hold position on which the base of the thumb abuts. Thereby, since the lock button is pushed in a direction of holding by the middle finger (or index finger), an operation with easy application of the force of the finger is performed, and the operation is stabilized with less fatigue.

In another structure example of the above-described holding mechanism, lock buttons having stoppers at their distal ends may be formed and used such that the stoppers engage and hold gears formed on the rotational shafts of the UD knob 10 and RL knob 11. In addition, aside from the holding mechanism constructed by these mechanical parts, a structure including an electrical driving system with use of a solenoid coil may be adopted.

As a first example, for instance, in the operation input portion body, a shaft portion, which is provided at a distal end thereof with an engaging portion for abutment on the rotational shaft, like the above-described engaging portion 51c of the shaft portion 51b, is axially movably supported.

The supporting of this shaft portion is implemented by projectingly forming a support frame within the operation input portion body, or by attaching an additional part. An annular permanent magnet is fitted and fixed on the shaft portion, and an electromagnet (solenoid coil), which annularly surrounds the permanent magnet with a gap, is configured to be fitted over the permanent magnet.

Further, a closed-loop circuit is constructed by the electromagnet, a magnet driving power supply which causes a driving current (direct current) to flow to the electromagnet, and an electric switch like the above-described switch 41. The electric switch is disposed at a position, like the position of the lock button 51 (52) on the operation input portion 2, and is operated by the second finger or third finger.

In this structure, by pushing the electric switch, a driving current flows from the magnet driving power supply to the electromagnet, the shaft portion on which the permanent magnet is provided moves, the engaging portion is abutted on the rotational shaft of the knob, and the rotational shaft is locked. By the locking of the rotational shaft, the bending operation of the bend portion, which is performed by the pulley and wire, is stopped, and the bending state is maintained. Further, if the electric switch is released, the electromagnetic force by the electromagnet is lost, the shaft portion moves, the engaging portion is separated from the rotational shaft of the knob, and the locked hold state is released.

In addition, a second example is described. In the above-described first example, the electric switch performs a momentary operation in which the locking of the rotational shaft is released if the electric switch is released. Thus, a structure in which an alternate operation can be performed may be adopted by adding a latch circuit to the closed-loop circuit which is composed of the electromagnet, magnet driving power supply and electric switch. Specifically, the latch circuit is operated by operating the electric switch, and the setting from OFF to ON is executed. The supply of current from the magnet driving power supply to the electromagnet is started and kept. Accordingly, by setting the latch circuit, the engaging portion is abutted on the rotational shaft of the knob, and the rotation is prohibited.

Next, if the latch circuit is operated by operating the electric switch, the reset from ON to OFF is executed, and the supply of current from the magnet driving power supply to the electromagnet is stopped. Accordingly, by resetting the latch circuit, the engaging portion is separated from the rotational shaft of the knob, and the rotation is set in the free state.

As has been described above, by mounting the holding mechanism in the operation input portion 2, the bend portion can be kept in a desired bending state at a time of observation, where necessary.

In addition, the holding mechanism performs, basically, a momentary operation by a switch operation. However, in the case of a mechanical mechanism, a structure in which an alternative operation can be performed may easily be implemented by applying a publicly-known rotary cam method or ratchet cam method. Furthermore, in the case of an electrical structure, a structure in which an alternative operation can be performed may be implemented by keeping the ON state of the switch, by making use of a bistable multivibrator such as a latch circuit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
    an insertion portion provided with a bend portion which bends in a first axial direction and a second axial direction perpendicular to the first axial direction;
    a first rotary body with a first rotational shaft, the first rotary body configured to rotate about the first rotational shaft upon operation input for bending the bend portion in the first axial direction;
    a first wire fixed to the bend portion and configured to be pulled and bend the bend portion in the first axial direction;
    a first pulling mechanism coupled to the first rotational shaft and configured to pull the first wire in interlock with rotation of the first rotary body;
    a second rotary body with a second rotational shaft provided coaxially with the first rotational shaft, the second rotary body configured to rotate about the first rotational shaft upon operation input for bending the bend portion in the second axial direction;
    a second wire fixed to the bend portion and configured to be pulled and bend the bend portion in the second axial direction;
    a driving source configured to generate a driving force for bending the bend portion in the second axial direction;
    a rotation amount detector configured to detect a rotation amount of the second rotary body;
    a second pulling mechanism comprising a rotary portion attached second wire to pull the second wire by rotating independently with respect to the second rotational shaft, the second pulling mechanism configured to pull the second wire in interlock with generation of the driving force by the driving source;
    a neutral position restoration mechanism comprising:
        an annular groove provided in the second rotary body and formed in an annular shape with a narrow-width groove serving as a middle position region formed in a part of the annular groove and having a narrower width than two ends of the annular groove;
        a fixing pin movable through the narrow-width groove such that the fixing pin is located at a center position of the narrow-width groove when the second rotary body is at a neutral position; and
        two moving spherical bodies disposed at the two ends of the annular groove and urged by a spring member;
    the neutral position restoration mechanism being configured to contract the spring member between one of the moving spherical bodies and the fixing pin in accordance with rotation of the second rotary body, and to push back the second rotary body when the second rotary body which has been rotated is released such that the fixing pin is returned to the middle position region by an urging force of the spring member, thereby restoring the second rotary body toward the neutral position thereof; and,
    a controller configured to output to the driving source a driving signal for bending the bend portion in the second axial direction, based on the rotation amount detected by the rotation amount detector.

2. The insertion device of claim 1, wherein the second rotary body has an outer periphery formed in a cylindrical shape.

3. The insertion device of claim 2, wherein a cylindrical side surface of the second rotary body forms any one of a cylindrical shape with a flat curved surface, a barrel shape with a convex curved surface, and an hourglass shape with a concave curved surface.

4. The insertion device of claim 2, wherein a slip prevention portion composed of a plurality of lines is formed on the cylindrical side surface of the second rotary body.

5. The insertion device of claim 1, wherein the first rotary body includes, on an outer surface thereof, a recess which forms a notch of a concave curved shape, the recess being formed such that a thumb of a hand, which holds the insertion portion and operates the first rotary body, extends beyond the recess and reaches a cylindrical side surface of the second rotary body.

6. The insertion device of claim 2, wherein the first rotary body includes, on an outer surface thereof, a recess which forms a notch of a concave curved shape, the recess having such a curvature and a size that a thumb of a hand, which holds the insertion portion and operates the first rotary body, is able to extend beyond the recess and to reach a cylindrical side surface of the second rotary body, and is able to perform a rotational operation of the second rotary body.

7. The insertion device of claim 5, wherein the first rotary body forms a disc shape with a plurality of the recesses formed on an outer surface thereof.

8. The insertion device of claim 1, further comprising an operation input portion body which is provided with a rotational shaft and accommodates the first pulling mechanism and the second pulling mechanism, and a motor as the driving source, wherein a speed adjusting switch configured to accelerate and decelerate a rotational speed of the motor is provided on the operation input portion body, and when the speed adjusting switch is not operated, the motor is rotated at a preset rotational speed, and the bend portion is bend-operated.

9. The insertion device of claim 1, further comprising an operation input portion body which is provided with a rotational shaft and accommodates the first pulling mechanism and the second pulling mechanism; and a holding mechanism including a first lock member configured to abut on a rotary shaft of the first rotary body and to prohibit the rotation of the first rotary body, and a second lock member configured to abut on a rotary shaft of the second rotary body and to prohibit the rotation of the second rotary body, wherein a bending state of the bend portion is kept by the first lock member and the second lock member.

* * * * *